US011661393B2

(12) United States Patent
Urata et al.

(10) Patent No.: US 11,661,393 B2
(45) Date of Patent: May 30, 2023

(54) METHOD OF PRODUCING A 2-((METH)ALLYLOXYMETHYL)ACRYLIC ACID DERIVATIVE, AND 2-((METH)ALLYLOXYMETHYL)ACRYLIC ACID ALKALI METAL SALT POWDER

(71) Applicant: NIPPON SHOKUBAI CO., LTD., Osaka (JP)

(72) Inventors: Minoru Urata, Osaka (JP); Kazuhiko Nakamura, Tokyo (JP); Jun Moteki, Chiba (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 115 days.

(21) Appl. No.: 16/944,554

(22) Filed: Jul. 31, 2020

(65) Prior Publication Data

US 2021/0032187 A1 Feb. 4, 2021

(30) Foreign Application Priority Data

Aug. 2, 2019 (JP) .............................. JP2019-142743
Aug. 2, 2019 (JP) .............................. JP2019-142744
Aug. 2, 2019 (JP) .............................. JP2019-142745

(51) Int. Cl.
*C07C 51/41* (2006.01)
*C07C 51/02* (2006.01)
*C07C 57/03* (2006.01)
*C07C 57/04* (2006.01)
*C07F 1/06* (2006.01)

(52) U.S. Cl.
CPC ............ *C07C 51/418* (2013.01); *C07C 51/02* (2013.01); *C07C 57/03* (2013.01); *C07F 1/06* (2013.01); *C07C 57/04* (2013.01)

(58) Field of Classification Search
CPC ......... C07C 67/11; C07C 51/02; C07C 69/54; C07C 51/418; C07C 57/04; C07C 57/54; C07C 59/60; C07C 57/03; C07F 1/06
USPC ....................................................... 562/500
See application file for complete search history.

(56) References Cited

U.S. PATENT DOCUMENTS

| | | | |
|---|---|---|---|
| 4,845,259 | A | 7/1989 | Arai et al. |
| 6,660,803 | B1 | 12/2003 | Yasuhara et al. |
| 8,796,492 | B2 | 8/2014 | Saito et al. |
| 9,499,466 | B2 | 11/2016 | Kaneko |
| 2012/0016095 | A1 | 1/2012 | Saito et al. |
| 2013/0197123 | A1 | 8/2013 | Kaneko |

FOREIGN PATENT DOCUMENTS

| | | |
|---|---|---|
| EP | 2626374 A1 | 8/2013 |
| JP | S63-179881 A | 7/1988 |
| JP | 2001-019663 A | 1/2001 |
| JP | 2004-231571 A | 8/2004 |
| JP | 2011-74068 A | 4/2011 |
| JP | 2011-137123 A | 7/2011 |
| JP | 2012-107208 A | 6/2012 |
| JP | 2013-194126 A | 9/2013 |

OTHER PUBLICATIONS

Extended European Search Report issued in corresponding European Patent Application No. 20188626.4 dated Dec. 15, 2020 (6 pages).

*Primary Examiner* — Ana Z Muresan
(74) *Attorney, Agent, or Firm* — Greenblum & Bernstein, P.L.C.

(57) ABSTRACT

Provided is a method of producing various 2-((meth)allyloxymethyl)acrylic acid derivatives in high yields with no need to load a raw material in a large excess for improving a reaction conversion ratio, and without use of a catalyst having high toxicity or a strong acid catalyst. Also provided are powder compounds that may be utilized as raw materials for synthesizing various chemical products. A method of producing a 2-((meth)allyloxymethyl)acrylic acid derivative includes causing the powder of a salt of a 2-((meth)allyloxymethyl)acrylic acid anion and an alkali metal cation (component A), and a halide (component B) to react with each other to produce a 2-((meth)allyloxymethyl)acrylic acid derivative. The 2-((meth)allyloxymethyl)acrylic acid alkali metal salt powder is the powder of a salt of a 2-((meth)allyloxymethyl)acrylic acid anion and an alkali metal cation, and has a bulk density of 0.50 g/mL or more, or a water content of 0.05 wt % or less.

6 Claims, No Drawings

METHOD OF PRODUCING A 2-((METH)ALLYLOXYMETHYL)ACRYLIC ACID DERIVATIVE, AND 2-((METH)ALLYLOXYMETHYL)ACRYLIC ACID ALKALI METAL SALT POWDER

BACKGROUND OF THE INVENTION

1. Field of the Invention

The present invention relates to a method of producing a 2-((meth)allyloxymethyl)acrylic acid derivative. The present invention also relates to a 2-((meth)allyloxymethyl) acrylic acid alkali metal salt powder.

2. Description of the Related Art

It has been known that a compound having a 2-((meth) allyloxymethyl)acryloyl group has high radical curability and shrinks to a small extent at the time of its curing, and a cured product obtained by curing the compound has excellent adhesiveness and excellent mechanical properties.

In Japanese Patent Application Laid-open No. 2011-137123, there is a disclosure of a high-boiling point compound having a 2-((meth)allyloxymethyl)acryloyl group. In Japanese Patent Application Laid-open No. 2011-74068, there is a disclosure of a compound having two or more 2-((meth)allyloxymethyl)acryloyl groups in one and the same molecule thereof. As methods of producing those compounds, there are disclosures of an ester exchange reaction between a lower ester of 2-((meth)allyloxymethyl) acrylic acid and an alcohol compound, and a dehydration esterification reaction between 2-((meth)allyloxymethyl) acrylic acid and an alcohol compound.

However, the ester exchange reaction is an equilibrium reaction, and hence the raw material ester needs to be loaded in a large excess for improving a reaction conversion ratio. Accordingly, there is a problem in that raw material cost increases or the raw material is liable to remain. In addition, the ester exchange reaction involves a problem in that a metal compound, such as a tin-containing compound having high toxicity, is required as a catalyst.

In addition, the dehydration esterification reaction involves a problem in that a reactor is required to have corrosion resistance because a strong acid is utilized as a catalyst.

Meanwhile, a (meth)acrylic acid metal salt, such as zinc (meth)acrylate or potassium (meth)acrylate, can introduce a metal into a compound such as a polymer or a cured product, which is obtained by using the (meth)acrylic acid metal salt, through use of an ionic bond between an anion derived from a carboxylic acid group (—COO⁻) and a metal cation. Accordingly, the (meth)acrylic acid metal salt can express various kinds of performance derived from at least one kind selected from the ionic bond between the metal ion and the carboxylic acid ion, and a metal species thereof, such as high hardness, high elasticity, high polarity, high ion exchangeability, and a high gas barrier property. The (meth)acrylic acid metal salt can express such various kinds of performance, and hence has been utilized in, for example, a cross-linking agent for a rubber to be used in a tire, a golf ball, or the like, a copolymerizable component for a polymer for a ship bottom paint, or a cross-linking agent to be used in the gas barrier layer of a gas barrier film (Japanese Patent Application Laid-open No. 2004-231571).

In addition, a (meth)acrylic acid alkali metal salt, such as potassium (meth)acrylate, has been utilized as a reaction raw material for producing an ester compound having a reactive (meth)acryloyl group (Japanese Patent Application Laid-open No. Sho 63-179881, Japanese Patent Application Laid-open No. 2001-019663, and Japanese Patent Application Laid-open No. 2013-194126).

The applicant has recently found and reported, as novel compounds that may be utilized as raw materials for synthesizing various chemical products, a diene-based carboxylic acid anion and a salt thereof (Japanese Patent Application Laid-open No. 2012-107208).

In general, when the handleability and the like of a novel compound are considered, the compound is preferably obtained as a pure product free of any solvent rather than being obtained in the state of a solution diluted with a solvent. Further, when the pure product is obtained as a solid, the solid is preferably a powder having a large bulk density because its handleability and loadability are improved, or the solid is preferably a powder having a small water content because when various chemical products, such as an ester compound, are synthesized by using the solid as a synthesis raw material, a side reaction can be suppressed, and hence their yields can be improved.

With regard to each of the diene-based carboxylic acid anion and an alkali metal salt thereof that are novel compounds, however, no investigations have been made on the properties of a pure product free of any solvent and a method of handling the pure product.

SUMMARY OF THE INVENTION

An object of the present invention is to provide a method by which various 2-((meth)allyloxymethyl)acrylic acid derivatives are produced in high yields with no need to load a raw material in a large excess for improving a reaction conversion ratio, and without use of a catalyst having high toxicity or a strong acid catalyst, and to provide a novel compound that is a powder having a large bulk density and a novel compound that is a powder having a small water content, the compounds being utilizable as raw materials for synthesizing various chemical products.

According to at least one embodiment of the present invention, three is provided a method of producing a 2-((meth)allyloxymethyl)acrylic acid derivative, the method including causing a powder of a salt of a 2-((meth)allyloxymethyl)acrylic acid anion represented by the general formula (1) and an alkali metal cation (component A), and a halide represented by the general formula (2) (component B) to react with each other to produce a 2-((meth)allyloxymethyl)acrylic acid derivative represented by the general formula (3):

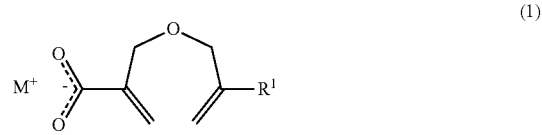

in the general formula (1), $R^1$ represents H or $CH_3$, and M represents an alkali metal;

in the general formula (2), $R^2$ represents an organic group or an organic-inorganic composite group, X represents a halogen group, and "n" represents a number of X groups bonded to $R^2$, and represents a number of 1 or more;

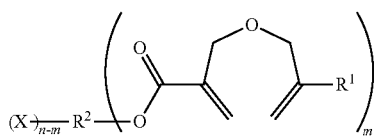

(3)

in the general formula (3), $R^1$ represents H or $CH_3$, $R^2$ represents an organic group or an organic-inorganic composite group, X represents a halogen group, and "m" represents a number of 2-((meth)allyloxymethyl)acryloyl groups bonded to $R^2$, and $n \geq m$ is satisfied.

In at least one exemplary embodiment of the present invention, the component A has a water content of 0.5 wt % or less.

In at least one exemplary embodiment of the present invention, the component A is obtained through a drying step with a spray dryer.

According to at least one embodiment of the present invention, three is provided a 2-((meth)allyloxymethyl) acrylic acid alkali metal salt powder, including a powder of a salt of a 2-((meth)allyloxymethyl)acrylic acid anion represented by the general formula (1) and an alkali metal cation, wherein the 2-((meth)allyloxymethyl)acrylic acid alkali metal salt powder has a bulk density of 0.50 g/mL or more:

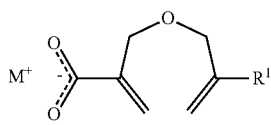

(1)

in the general formula (1), $R^1$ represents H or $CH_3$, and M represents an alkali metal.

According to at least one embodiment of the present invention, three is provided a method of producing a 2-((meth)allyloxymethyl)acrylic acid alkali metal salt powder that is a powder having a bulk density of 0.50 g/mL or more, the method including a drying step of performing drying with a conduction heat transfer drying apparatus.

According to at least one embodiment of the present invention, three is provided a 2-((meth)allyloxymethyl) acrylic acid alkali metal salt powder, including a powder of a salt of a 2-((meth)allyloxymethyl)acrylic acid anion represented by the general formula (1) and an alkali metal cation, wherein the 2-((meth)allyloxymethyl)acrylic acid alkali metal salt powder has a water content of 0.5 wt % or less:

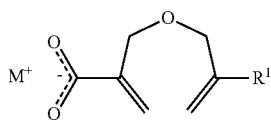

(1)

in the general formula (1), $R^1$ represents H or $CH_3$, and M represents an alkali metal.

According to at least one embodiment of the present invention, three is provided a method of producing a 2-((meth)allyloxymethyl)acrylic acid alkali metal salt powder that is a powder having a water content of 0.5 wt % or less, the method including a drying step of performing drying with a convection heat transfer drying apparatus.

According to at least one embodiment of the present invention, there can be provided the method by which various 2-((meth)allyloxymethyl)acrylic acid derivatives are produced in high yields with no need to load a raw material in a large excess for improving a reaction conversion ratio, and without use of a catalyst having high toxicity or a strong acid catalyst.

According to at least one embodiment of the present invention, there can be provided the novel compound that is a powder having a large bulk density, the compound being utilizable as a raw material for synthesizing various chemical products. The 2-((meth)allyloxymethyl)acrylic acid alkali metal salt powder according to at least one embodiment of the present invention is a powder having a large bulk density. Accordingly, the powder is excellent in handleability and loadability, and hence its range of utilization as a raw material for synthesizing various chemical products may expand.

According to at least one embodiment of the present invention, there can be provided the novel compound that is a powder having a small water content, the compound being utilizable as a raw material for synthesizing various chemical products. The 2-((meth)allyloxymethyl)acrylic acid alkali metal salt powder according to at least one embodiment of the present invention is a powder having a small water content. Accordingly, when various chemical products are synthesized by using the powder as a synthesis raw material, a side reaction can be suppressed, and hence their yields can be improved. Therefore, the range of utilization of the 2-((meth)allyloxymethyl)acrylic acid alkali metal salt powder according to at least one embodiment of the present invention as a raw material for synthesizing various chemical products may expand.

DESCRIPTION OF THE EMBODIMENTS

When the term "mass" (commonly used as an SI unit for representing a weight) is used in this specification, the term may be replaced with the term "weight" that has heretofore been commonly used in general as a unit for a weight.

A combination of two or more individual preferred modes of the present invention described below is also a preferred mode of the present invention.

<<<<1. Method of Producing 2-((Meth)Allyloxymethyl) Acrylic Acid Derivative>>>>

A method of producing a 2-((meth)allyloxymethyl)acrylic acid derivative according to at least one embodiment of the present invention includes causing the powder of a salt of a 2-((meth)allyloxymethyl)acrylic acid anion and an alkali metal cation (component A), and a halide (component B) to react with each other. When the powder of the salt of the 2-((meth)allyloxymethyl)acrylic acid anion and the alkali metal cation (component A), and the halide (component B) are caused to react with each other, various 2-((meth)allyloxymethyl)acrylic acid derivatives can be produced in high yields with no need to load a raw material in a large excess for improving a reaction conversion ratio, and without use of a catalyst having high toxicity or a strong acid catalyst.

<<1-1. Powder of Salt of 2-((Meth)Allyloxymethyl) Acrylic Acid Anion and Alkali Metal Cation (Component A)>>

The component A is the powder of the salt of the 2-((meth)allyloxymethyl)acrylic acid anion and the alkali metal cation, that is, a 2-((meth)allyloxymethyl)acrylic acid alkali metal salt powder.

The component A is represented by the general formula (1).

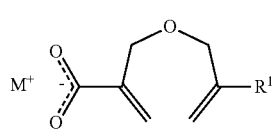

(1)

In the general formula (1), $R^1$ represents H or $CH_3$, and M represents an alkali metal.

In the general formula (1), the bond "oxygen atom-carbon atom-oxygen atom" that is shown to be a monovalent anion as a result of the bonding of atoms by bonds represented by both of a dotted line and a solid line is preferably such that the two bonds "carbon atom-oxygen atom" in the bond are equivalent to each other, and hence the entirety of the bond "oxygen atom-carbon atom-oxygen atom" serves as a monovalent anion.

Any appropriate alkali metal may be adopted as the alkali metal M constituting the component A. Specific examples of the alkali metal include lithium, sodium, potassium, rubidium, cesium, and francium. Of those alkali metals, from the viewpoints of, for example, ease of handling, ease of synthesis, and low cost, the alkali metal M is preferably lithium, sodium, or potassium, more preferably sodium or potassium, most preferably potassium.

The component A is a "powder". Herein, the term "powder" to be used in the description of the present invention refers to a form defined as a solid that may be handled as an aggregate of grains, such as a so-called granule, or an aggregate of powders of shapes smaller than the grains.

The water content of the component A is preferably 0.5 wt % or less, more preferably 0.2 wt % or less, still more preferably 0.1 wt % or less, particularly preferably 0.05 wt % or less. When the water content of the component A is small as described above, in the method of producing a 2-((meth)allyloxymethyl)acrylic acid derivative according to at least one embodiment of the present invention, a side reaction can be suppressed, and hence the yield of the derivative can be improved.

The bulk density (unit: g/mL) (also referred to as "bulk specific gravity" (no unit)) of the component A is preferably 0.01 g/mL or more, more preferably 0.1 g/mL or more, still more preferably 0.2 g/mL or more, particularly preferably 0.25 g/mL or more. When the bulk density of the component A is large as described above, the component may be excellent in handleability and loadability. Therefore, in, for example, the method of producing a 2-((meth)allyloxymethyl)acrylic acid derivative according to at least one embodiment of the present invention, the handleability and loadability of the component A serving as a raw material may be excellent.

The component A may be preferably produced by a production method including: a solution-preparing step of obtaining a solution of a 2-((meth)allyloxymethyl)acrylic acid alkali metal salt; and a drying step of performing drying with a drying apparatus.

A method described in Japanese Patent Application Laid-open No. 2012-107208, which has been reported by the applicant in advance, may be incorporated for the solution-preparing step of obtaining the solution of the 2-((meth)allyloxymethyl)acrylic acid alkali metal salt.

In the drying step of performing drying with the drying apparatus, the solution of the 2-((meth)allyloxymethyl)acrylic acid alkali metal salt obtained in the solution-preparing step of obtaining the solution is preferably dried to provide the 2-((meth)allyloxymethyl)acrylic acid alkali metal salt powder.

Any appropriate drying apparatus may be used in the drying step of performing drying with the drying apparatus to such an extent that the effects of the present invention are not impaired. Drying apparatus may be classified by a method of applying heat to a drying object, and are typically classified into a convection heat transfer drying apparatus, a conduction heat transfer drying apparatus, and a radiation heat transfer drying apparatus.

Examples of the convection heat transfer drying apparatus include a box dryer, a band dryer, a tunnel dryer, a nozzle jet dryer, a through-flow vertical dryer, a rotary dryer, a fluidized bed dryer, a flash dryer, and a spray dryer.

Examples of the conduction heat transfer drying apparatus include a box dryer, a disc dryer, a gutter-type or cylindrical stirring dryer, an inversely conical stirring dryer, a rotary dryer (a cylindrical rotary dryer or a double cone rotary dryer), and a cylindrical dryer.

Drying conditions in the drying step only need to be appropriately set in accordance with the drying apparatus to be used.

At the time of the production of the component A, the component is preferably produced by a production method including a drying step of performing drying with a convection heat transfer drying apparatus because the effects of the present invention can be further expressed.

<1-1-1. 2-((Meth)Allyloxymethyl)Acrylic Acid Alkali Metal Salt Powder (X)>

A 2-((meth)allyloxymethyl)acrylic acid alkali metal salt powder (X) according to at least one embodiment of the present invention includes a powder of a salt of a 2-((meth)allyloxymethyl)acrylic acid anion represented by the general formula (1) and an alkali metal cation, wherein the 2-((meth)allyloxymethyl)acrylic acid alkali metal salt powder has a bulk density of 0.50 g/mL or more.

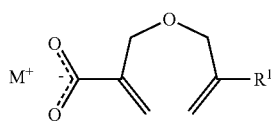

(1)

In the general formula (1), $R^1$ represents H or $CH_3$, and M represents an alkali metal.

The bulk density of the 2-((meth)allyloxymethyl)acrylic acid alkali metal salt powder (X) according to at least one embodiment of the present invention is preferably from 0.55 g/mL to 0.95 g/mL, more preferably from 0.60 g/mL to 0.95 g/mL, still more preferably from 0.63 g/mL to 0.95 g/mL. When the bulk density of the powder is large as described above, the powder may be excellent in handleability and loadability. Therefore, for example, the range of utilization of the 2-((meth)allyloxymethyl)acrylic acid alkali metal salt powder (X) according to at least one embodiment of the present invention as a raw material for synthesizing various chemical products may expand.

The primary particle diameter of the 2-((meth)allyloxymethyl)acrylic acid alkali metal salt powder (X) according to at least one embodiment of the present invention is preferably from 10 μm to 5,000 μm, more preferably from 30 μm to 4,000 μm, still more preferably from 50 μm to 3,000 μm, particularly preferably from 100 μm to 2,000 μm. When the primary particle diameter of the powder falls within the ranges, the powder may be more excellent in handleability and loadability. Therefore, for example, the range of utilization of the 2-((meth)allyloxymethyl)acrylic acid alkali metal salt powder (X) according to at least one embodiment of the present invention as a raw material for synthesizing various chemical products may further expand.

The water content of the 2-((meth)allyloxymethyl)acrylic acid alkali metal salt powder (X) according to at least one embodiment of the present invention is preferably 1.0 wt % or less, more preferably 0.5 wt % or less, still more preferably 0.3 wt % or less, particularly preferably 0.2 wt % or less. When the water content of the powder is small as described above, the 2-((meth)allyloxymethyl)acrylic acid alkali metal salt powder (X) according to at least one embodiment of the present invention can further express characteristics as a powder.

The 2-((meth)allyloxymethyl)acrylic acid alkali metal salt powder (X) according to at least one embodiment of the present invention may contain a 2-((meth)allyloxymethyl)acrylic acid alkali metal salt, and as an optional component, a component except water. Any appropriate optional component may be adopted as the optional component to such an extent that the effects of the present invention are not impaired. Examples of such optional component include: 2-((meth)allyloxymethyl)acrylic acid; a salt of 2-((meth)allyloxymethyl)acrylic acid and a metal except an alkali metal; a 2-((meth)allyloxymethyl)acrylic acid ester; a salt of an anion except a 2-((meth)allyloxymethyl)acrylic acid anion and a metal cation; a salt of an anion except a 2-((meth)allyloxymethyl)acrylic acid anion and a nonmetal cation; a polymerization inhibitor; an antioxidant; an antiseptic; and a surfactant. The 2-((meth)allyloxymethyl)acrylic acid alkali metal salt powder (X) according to at least one embodiment of the present invention contains, for example, preferably 1 wt % or more and 100 wt % or less, more preferably 50 wt % or more and 100 wt % or less, still more preferably 90 wt % or more and 100 wt % or less of the salt of the 2-((meth)allyloxymethyl)acrylic acid anion represented by the general formula (1) and the alkali metal cation.

The 2-((meth)allyloxymethyl)acrylic acid alkali metal salt powder (X) according to at least one embodiment of the present invention may be preferably produced by a production method including: a solution-preparing step of obtaining a solution of the 2-((meth)allyloxymethyl)acrylic acid alkali metal salt; and a drying step of performing drying with a drying apparatus.

A method described in Japanese Patent Application Laid-open No. 2012-107208, which has been reported by the applicant in advance, may be incorporated for the solution-preparing step of obtaining the solution of the 2-((meth)allyloxymethyl)acrylic acid alkali metal salt.

In the drying step of performing drying with the drying apparatus, the solution of the 2-((meth)allyloxymethyl)acrylic acid alkali metal salt obtained in the solution-preparing step of obtaining the solution is preferably dried to provide the 2-((meth)allyloxymethyl)acrylic acid alkali metal salt powder.

Any appropriate drying apparatus may be used in the drying step of performing drying with the drying apparatus to such an extent that the effects of the present invention are not impaired. Drying apparatus may be classified by a method of applying heat to a drying object, and are typically classified into a convection heat transfer drying apparatus, a conduction heat transfer drying apparatus, and a radiation heat transfer drying apparatus.

Examples of the convection heat transfer drying apparatus include a box dryer, a band dryer, a tunnel dryer, a nozzle jet dryer, a through-flow vertical dryer, a rotary dryer, a fluidized bed dryer, a flash dryer, and a spray dryer.

Examples of the conduction heat transfer drying apparatus include a box dryer, a disc dryer, a gutter-type or cylindrical stirring dryer, an inversely conical stirring dryer, a rotary dryer (a cylindrical rotary dryer or a double cone rotary dryer), and a cylindrical dryer.

Drying conditions in the drying step only need to be appropriately set in accordance with the drying apparatus to be used.

At the time of the production of the 2-((meth)allyloxymethyl)acrylic acid alkali metal salt powder (X) according to at least one embodiment of the present invention, the powder is preferably produced by a production method including a drying step of performing drying with a conduction heat transfer drying apparatus because the effects of the present invention can be further expressed.

<1-1-2. 2-((Meth)Allyloxymethyl)Acrylic Acid Alkali Metal Salt Powder (Y)>

A 2-((meth)allyloxymethyl)acrylic acid alkali metal salt powder (Y) according to at least one embodiment of the present invention includes a powder of a salt of a 2-((meth)allyloxymethyl)acrylic acid anion represented by the general formula (1) and an alkali metal cation, wherein the 2-((meth)allyloxymethyl)acrylic acid alkali metal salt powder has a water content of 0.05 wt % or less.

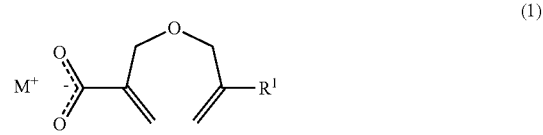

(1)

In the general formula (1), $R^1$ represents H or $CH_3$, and M represents an alkali metal.

The water content of the 2-((meth)allyloxymethyl)acrylic acid alkali metal salt powder (Y) according to at least one embodiment of the present invention is preferably 0.03 wt % or less, more preferably 0.02 wt % or less, still more preferably 0.01 wt % or less. In the case where the water content of the powder is small as described above, when various chemical products are synthesized by using the powder as a synthesis raw material, a side reaction can be suppressed, and hence their yields can be improved. Therefore, the range of utilization of the 2-((meth)allyloxymethyl)acrylic acid alkali metal salt powder (Y) according to at least one embodiment of the present invention as a raw material for synthesizing various chemical products may expand.

The lower limit value of the primary particle diameter of the 2-((meth)allyloxymethyl)acrylic acid alkali metal salt powder (Y) according to at least one embodiment of the present invention is preferably 0.1 μm or more, more preferably 0.5 μm or more, still more preferably 1.0 μm or more, particularly preferably 5.0 μm or more. In addition, the upper limit value of the primary particle diameter is preferably 200 μm or less, more preferably 150 μm or less, still more preferably 100 μm or less, particularly preferably 50 μm or less. When the primary particle diameter of the powder falls within the ranges, the water content of the powder can be further reduced. Accordingly, when various chemical products are synthesized by using such powder as a synthesis raw material, a side reaction can be further suppressed, and hence their yields can be further improved. Therefore, the range of utilization of the 2-((meth)allyloxymethyl)acrylic acid alkali metal salt powder (Y) according to at least one embodiment of the present invention as a raw material for synthesizing various chemical products may further expand.

The lower limit value of the bulk density of the 2-((meth)allyloxymethyl)acrylic acid alkali metal salt powder (Y) according to at least one embodiment of the present invention is preferably 0.1 g/mL or more, more preferably 0.15/mL or more, still more preferably 0.20 g/mL or more, particularly preferably 0.25 g/mL or more. In addition, the upper limit value of the bulk density is preferably 0.8 g/mL or less, more preferably 0.7 g/mL or less, still more preferably 0.6 g/mL or less. When the bulk density of the powder is large as described above, the powder may be excellent in handleability and loadability. Therefore, for example, the range of utilization of the 2-((meth)allyloxymethyl)acrylic acid alkali metal salt powder (Y) according to at least one embodiment of the present invention as a raw material for synthesizing various chemical products may expand.

The 2-((meth)allyloxymethyl)acrylic acid alkali metal salt powder (Y) according to at least one embodiment of the present invention may contain a 2-((meth)allyloxymethyl)acrylic acid alkali metal salt, and as an optional component, a component except water. Any appropriate optional component may be adopted as the optional component to such an extent that the effects of the present invention are not impaired. Examples of such optional component include: 2-((meth)allyloxymethyl)acrylic acid; a salt of 2-((meth)allyloxymethyl)acrylic acid and a metal except an alkali metal; a 2-((meth)allyloxymethyl)acrylic acid ester; a salt of an anion except a 2-((meth)allyloxymethyl)acrylic acid anion and a metal cation; a salt of an anion except a 2-((meth)allyloxymethyl)acrylic acid anion and a nonmetal cation; a polymerization inhibitor; an antioxidant; an antiseptic; and a surfactant. The 2-((meth)allyloxymethyl)acrylic acid alkali metal salt powder (Y) according to at least one embodiment of the present invention contains, for example, preferably 1 wt % or more and 100 wt % or less, more preferably 50 wt % or more and 100 wt % or less, still more preferably 90 wt % or more and 100 wt % or less of the salt of the 2-((meth)allyloxymethyl)acrylic acid anion represented by the general formula (1) and the alkali metal cation.

The 2-((meth)allyloxymethyl)acrylic acid alkali metal salt powder (Y) according to at least one embodiment of the present invention may be preferably produced by a production method including: a solution-preparing step of obtaining a solution of the 2-((meth)allyloxymethyl)acrylic acid alkali metal salt; and a drying step of performing drying with a drying apparatus.

A method described in Japanese Patent Application Laid-open No. 2012-107208, which has been reported by the applicant in advance, may be incorporated for the solution-preparing step of obtaining the solution of the 2-((meth)allyloxymethyl)acrylic acid alkali metal salt.

In the drying step of performing drying with the drying apparatus, the solution of the 2-((meth)allyloxymethyl)acrylic acid alkali metal salt obtained in the solution-preparing step of obtaining the solution is preferably dried to provide the 2-((meth)allyloxymethyl)acrylic acid alkali metal salt powder.

Any appropriate drying apparatus may be used in the drying step of performing drying with the drying apparatus to such an extent that the effects of the present invention are not impaired. Drying apparatus may be classified by a method of applying heat to a drying object, and are typically classified into a convection heat transfer drying apparatus, a conduction heat transfer drying apparatus, and a radiation heat transfer drying apparatus.

Examples of the convection heat transfer drying apparatus include a box dryer, a band dryer, a tunnel dryer, a nozzle jet dryer, a through-flow vertical dryer, a rotary dryer, a fluidized bed dryer, a flash dryer, and a spray dryer.

Examples of the conduction heat transfer drying apparatus include a box dryer, a disc dryer, a gutter-type or cylindrical stirring dryer, an inversely conical stirring dryer, a rotary dryer (a cylindrical rotary dryer or a double cone rotary dryer), and a cylindrical dryer.

Drying conditions in the drying step only need to be appropriately set in accordance with the drying apparatus to be used.

At the time of the production of the 2-((meth)allyloxymethyl)acrylic acid alkali metal salt powder (Y) according to at least one embodiment of the present invention, the powder is preferably produced by a production method including a drying step of performing drying with a convection heat transfer drying apparatus because the effects of the present invention can be further expressed.

<<1-2. Halide (Component B)>>

The component B is a halide.

The component B is represented by the general formula (2).

$$R^2\!\!-\!\!(X)_n \qquad (2)$$

In the general formula (2), $R^2$ represents an organic group or an organic-inorganic composite group, X represents a halogen group, and "n" represents the number of X groups bonded to $R^2$, and represents a number of 1 or more.

Any appropriate halogen group may be adopted as X to such an extent that the effects of the present invention are not impaired. Examples of such halogen group include a chlorine group, a bromine group, and an iodine group. Of those, a bromine group or an iodine group is preferred.

Any appropriate organic group or organic-inorganic composite group may be adopted as $R^2$ to such an extent that the effects of the present invention are not impaired.

Examples of the organic group include an organic group free of any heteroatom and an organic group having a heteroatom.

Examples of the organic group free of any heteroatom include a linear saturated hydrocarbon group, a linear unsaturated hydrocarbon group, a branched saturated hydrocarbon group, and a branched unsaturated hydrocarbon group.

Examples of the organic group having a heteroatom include: an organic group obtained by substituting part of a linear saturated hydrocarbon group with a heteroatom; a linear saturated hydrocarbon group having a substituent containing a heteroatom; an organic group obtained by substituting part of a linear unsaturated hydrocarbon group with a heteroatom; a linear unsaturated hydrocarbon group having a substituent containing a heteroatom; an organic group obtained by substituting part of a branched saturated hydrocarbon group with a heteroatom; a branched saturated hydrocarbon group having a substituent containing a heteroatom; an organic group obtained by substituting part of a branched unsaturated hydrocarbon group with a heteroatom; and a branched unsaturated hydrocarbon group having a substituent containing a heteroatom.

The organic-inorganic composite group is, for example, such a silicon-containing organic group as described later.

<<1-3. Details of Method of Producing 2-((Meth)Allyloxymethyl)Acrylic Acid Derivative>>

A method of producing a 2-((meth)allyloxymethyl)acrylic acid derivative according to at least one embodiment of the present invention includes causing the powder of the salt of the 2-((meth)allyloxymethyl)acrylic acid anion and the alkali metal cation (component A), and the halide (component B) described above to react with each other. According to this method, various 2-((meth)allyloxymethyl)acrylic acid derivatives can be produced in high yields with no need to load a raw material in a large excess for improving a reaction conversion ratio, and without use of a catalyst having high toxicity or a strong acid catalyst.

For example, when the component A having a small water content is adopted in the method of producing a 2-((meth) allyloxymethyl)acrylic acid derivative according to at least one embodiment of the present invention, a side reaction resulting from the presence of water can be suppressed, and hence the yield of the 2-((meth)allyloxymethyl)acrylic acid derivative can be improved.

When a polyfluoroalkyl iodide is adopted as the component B, a 2-((meth)allyloxymethyl)acrylic acid polyfluoroalkyl ester may be produced.

In general, a reaction in which a carboxylic acid alkali metal salt ($R^a$-LOOM: $R^a$ represents an organic group and M represents an alkali metal atom) and an organic halide ($R^b$—X: $R^b$ represents an organic group and X represents a halogen atom) are caused to react with each other to provide a carboxylic acid derivative ($R^a$—COO$R^b$) is often inhibited by water, and a reduction in yield of the 2-((meth)allyloxymethyl)acrylic acid derivative or the like may be caused by a side reaction or the like (e.g., Japanese Patent Application Laid-open No. 2011-137123). In the method of producing a 2-((meth)allyloxymethyl)acrylic acid derivative according to at least one embodiment of the present invention, however, the component A having a small water content may be adopted as a raw material. In this case, a side reaction resulting from the presence of water can be suppressed, and hence the yield of the 2-((meth)allyloxymethyl)acrylic acid derivative can be improved.

For example, when such a silicon-containing organic halide as represented by the general formula (4) ($R^2$ in the general formula (2) corresponds to an organic-inorganic composite group) is adopted as the component B, a compound that is a 2-((meth)allyloxymethyl)acrylic acid ester having a silicon-containing organic group introduced into its ester moiety may be produced.

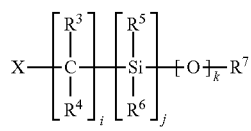

(4)

In the general formula (4), $R^3$, $R^4$, and $R^7$ each represent a hydrogen atom or an alkyl group, $R^5$ and $R^6$ each represent an alkyl group, an alkoxide group, or a siloxane group, "i" represents an integer of from 1 to 3, "j" represents an integer of 1 or more, and "k" represents 0 or 1.

In the general formula (4), X represents a halogen group as in that described above. Any appropriate halogen group may be adopted as X to such an extent that the effects of the present invention are not impaired. Examples of such halogen group include a chlorine group, a bromine group, and an iodine group. Of those, a bromine group or an iodine group is preferred.

EXAMPLES

The present invention is specifically described below by way of Examples, but the present invention is not limited to these Examples. "Part(s)" means "part(s) by weight" and "%" means "wt %" unless otherwise specified.

<Bulk Density>

Measurement was performed with an apparent density-measuring device in conformity with JIS K 3362.

<Water Content>

A Karl Fischer water titrator (manufactured by Kyoto Electronics Manufacturing Co., Ltd., "MKC-510") was used as a measuring apparatus, and "HYDRANAL COULOMAT CG" and "HYDRANAL COULOMAT A" manufactured by Fluka were used as a counter solution and a generating solution, respectively.

<Analysis of Reaction Liquid by Gas Chromatography (GC)>

A reaction solution was diluted with acetonitrile, and the diluted solution was analyzed with the following gas chromatography apparatus, followed by the calculation of the ratio of a produced compound based on a peak area ratio.
GC apparatus: GC-2025 (manufactured by Shimadzu Corporation)
Separation column: CAPILLARY COLUMN DB-1 (manufactured by Agilent Technologies, measuring 30 m in length by 0.25 mm in inner diameter, thickness: 0.25 μm)

<Analysis of Reaction Liquid by High Performance Liquid Chromatography (HPLC)>

A reaction solution was diluted with the following diluent solvent, and the diluted solution was analyzed with the following high performance liquid chromatography (HPLC) apparatus and under the following conditions, followed by the calculation of the ratio of a produced compound based on a peak area ratio.
HPLC apparatus: The combination of DGU-20A5, LC-20AD, SIL-20A, SPD-20A, CTO-20A, and RID-10 (each of which is manufactured by Shimadzu Corporation)
Elution solvent: A mixed solvent containing a 0.1 mol % aqueous solution of phosphoric acid and acetonitrile at 50/50 (vol %), 1.0 mL/min
Separation column: CAPCELL PAK TYPE:ADME (manufactured by Shiseido Company, Limited, particle diameter: 5 microns, measuring 4.6 mm in inner diameter by 150 mm in length)

[Synthesis Example 1]: Synthesis of Aqueous Solution of Salt of 2-(Allyloxymethyl)Acrylic Acid Ion and Potassium Ion 809.1 Parts of a 4.44 wt % aqueous solution of potassium hydroxide and 100.0 parts of methyl 2-(allyloxymethyl) acrylate containing 300 ppm of 6-tert-butyl-2,4-xylenol were loaded into a reactor having incorporated thereinto a magnetic stirrer, and were stirred with the magnetic stirrer while being cooled in a water bath so that a solution temperature became 35° C. or less. The stirring was continued for 4 hours to provide an aqueous solution (1)

containing 12.7 wt % of a salt of a 2-(allyloxymethyl)acrylic acid ion and a potassium ion.

[Example 1]: Synthesis of Potassium 2-(Allyloxymethyl)Acrylate Powder

The aqueous solution (1) obtained in Synthesis Example 1 was concentrated under reduced pressure with an evaporator to prepare an aqueous solution containing 50 wt % of potassium 2-(allyloxymethyl)acrylate, and then the solution was subjected to spray drying with a spray drying apparatus (manufactured by Yamato Scientific Co., Ltd., PULVIS MINI SPRAY, model: GA-32, cyclone single-point collection type). The spray nozzle of the apparatus was a two-fluid nozzle, and its raw material supply amount was 0.64 kg/h. As a result of continuous spray drying of the solution under the conditions of a pressurized air pressure of 2.0 kgf/cm², an air capacity of 0.42 m³/min, an inlet hot air temperature of 190° C., and an outlet temperature of 100° C. for 0.4 hour, 0.085 kg of a potassium 2-(allyloxymethyl)acrylate powder having a bulk density of 0.29 g/mL and a water content of 0.031 wt % was obtained. The recovery ratio of the powder was 66 wt %.

[Example 2]

19.83 Kilograms of the aqueous solution (1) obtained in Synthesis Example 1 was dried with a conduction heat transfer drying apparatus. Specifically, as a result of the drying of the solution with an 80-liter vacuum kneader under stirring and under the conditions of a jacket temperature of 40° C. and a pressure of from 34 Torr to 111 Torr for 35 hours, 2.37 kg of a potassium 2-(allyloxymethyl)acrylate powder having a bulk density of 0.64 g/mL and a water content of 0.19 wt % was obtained. The recovery ratio of the powder was 94 wt %.

[Example 3]: Production of 1H,1H,2H,2H-Nonafluorohexyl Ester of 2-(Allyloxymethyl)Acrylic Acid The potassium 2-(allyloxymethyl)acrylate powder obtained in Example 1 (6.00 g, containing 0.031 wt % of water), tert-butyl alcohol (12.00 g, containing 0.070 wt % of water, manufactured by Wako Pure Chemical Industries, Ltd., special grade reagent), 1H,1H,2H,2H-nonafluorohexyl iodide (11.99 g, manufactured by Tokyo Chemical Industry Co., Ltd.), POLYSTOP 7300P (0.010 g, manufactured by Hakuto Co., Ltd.), 6-tert-butyl-2,4-xylenol (0.096 g, manufactured by Tokyo Chemical Industry Co., Ltd.), and a magnetic stirrer were loaded into an autoclave reactor, and a gas phase portion was purged with a nitrogen gas containing 7 vol % of oxygen. After that, the mixture was heated in an oil bath at 180° C. under stirring with the magnetic stirrer. The mixture was subjected to a reaction for 6 hours, and then the reaction liquid was subjected to GC analysis. As a result, the peak of 1H,1H,2H,2H-nonafluorohexyl iodide that was a raw material disappeared, and a new product peak was observed. The area percentage of the product peak was 88%.

[Example 4]: Production of 1,6-Bis(2-(Allyloxymethyl)Acryloyl)Hexane

The potassium 2-(allyloxymethyl)acrylate powder obtained in Example 1 (6.00 g, containing 0.031 wt % of water), tert-butyl alcohol (12.00 g, containing 0.070 wt % of water, manufactured by Wako Pure Chemical Industries, Ltd., special grade reagent), 1,6-dibromohexane (11.99 g, manufactured by Tokyo Chemical Industry Co., Ltd.), 6-tert-butyl-2,4-xylenol (0.096 g, manufactured by Tokyo Chemical Industry Co., Ltd.), and a magnetic stirrer were loaded into an autoclave reactor, and a gas phase portion was purged with a nitrogen gas containing 7 vol % of oxygen. After that, the mixture was heated in an oil bath at 90° C. under stirring with the magnetic stirrer. The mixture was subjected to a reaction for 4 hours, and then the reaction liquid was subjected to HPLC analysis. As a result, the peak of 1,6-H,2H,2H-nonafluorohexyl iodide that was a raw material (peak A: retention time: 18.07 minutes) reduced, and two kinds of product peaks (peak B: retention time: 26.1 minutes, peak C: retention time: 37.1 minutes) were observed with a RI detector. The area ratio "peak A:peak B:peak C" was 29:52:19. The reaction liquid was further subjected to a reaction in an oil bath at 120° C. for 4 hours, and then the resultant reaction liquid was subjected to HPLC analysis. As a result, the peak A and the product peak B disappeared, and only the product peak C was observed with the RI detector.

According to the method of producing a 2-((meth)allyloxymethyl)acrylic acid derivative according to at least one embodiment of the present invention, there can be provided the method by which various 2-((meth)allyloxymethyl)acrylic acid derivatives are produced in high yields with no need to load a raw material in a large excess for improving a reaction conversion ratio, and without use of a catalyst having high toxicity or a strong acid catalyst, and any such 2-((meth)allyloxymethyl)acrylic acid derivative may be widely utilized as a raw material for synthesizing various chemical products.

The 2-((meth)allyloxymethyl)acrylic acid alkali metal salt powder (X) according to at least one embodiment of the present invention is a powder having a large bulk density. Accordingly, the powder is excellent in handleability and loadability, and hence may be widely utilized as a raw material for synthesizing various chemical products, such as an ester compound.

The 2-((meth)allyloxymethyl)acrylic acid alkali metal salt powder (Y) according to at least one embodiment of the present invention is a powder having a small water content. Accordingly, when various chemical products are synthesized by using the powder as a synthesis raw material, a side reaction can be suppressed, and hence their yields can be improved. Accordingly, the powder may be widely utilized as a raw material for synthesizing various chemical products, such as an ester compound.

What is claimed is:

1. A method of producing a 2-((meth)allyloxymethyl)acrylic acid derivative, the method comprising: reacting
   (i) a powder of a salt of a 2-((meth)allyloxymethyl)acrylic acid anion represented by the general formula (1) and an alkali metal cation (component A), and
   (ii) a halide represented by the general formula (2) (component B)
with each other to produce a 2-((meth)allyloxymethyl)acrylic acid derivative represented by the general formula (3):

wherein:

(1)

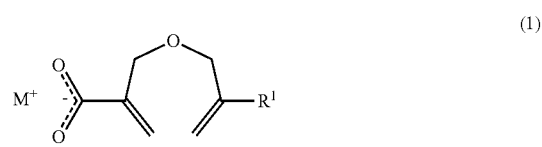

in the general formula (1), $R^1$ represents H or $CH_3$, and M represents an alkali metal;

$$R^2\text{-}(X)_n \qquad (2)$$

in the general formula (2), $R^2$ represents a polyfluoroalkyl group, X represents a halogen group selected from the group consisting of a chlorine group, a bromine group, and an iodine group, and "n" represents a number of X groups bonded to $R^2$, and represents a number of 1 or more; and

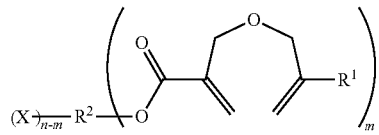
(3)

in the general formula (3), $R^1$ represents H or $CH_3$, $R^2$ represents a polyfluoroalkyl group, X represents a halogen group selected from the group consisting of a chlorine group, a bromine group, and an iodine group, "m" represents a number of 2-((meth)allyloxymethyl)acryloyl groups bonded to $R^2$, and n≥m is satisfied.

2. The method of producing a 2-((meth)allyloxymethyl)acrylic acid derivative according to claim 1, wherein the component A has a water content of 0.5 wt % or less.

3. The method of producing a 2-((meth)allyloxymethyl)acrylic acid derivative according to claim 1, wherein the component A is obtained through a drying step with a spray dryer.

4. A method of producing a 2-((meth)allyloxymethyl)acrylic acid derivative, the method comprising: reacting
   (i) a powder of a salt of a 2-((meth)allyloxymethyl)acrylic acid anion represented by the general formula (1) and an alkali metal cation (component A), and
   (ii) a halide represented by the general formula (4) (component B)
with each other to produce a 2-((meth)allyloxymethyl)acrylic acid derivative
wherein:

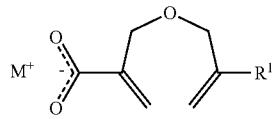
(1)

in the general formula (1), $R^1$ represents H or $CH_3$, and M represents an alkali metal;

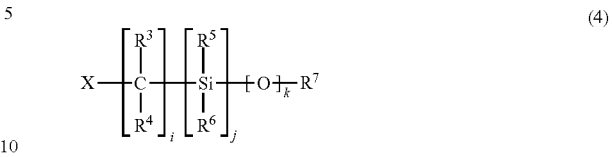
(4)

in the general formula (4), $R^3$, $R^4$, and $R^7$ each represent a hydrogen atom or an alkyl group, $R^5$ and $R^6$ each represent an alkyl group, an alkoxide group, or a siloxane group, "i" represents an integer of from 1 to 3, "j" represents an integer of 1 or more, "k" represents 0 or 1; and X represents a halogen group selected from the group consisting of a chlorine group, a bromine group, and an iodine group; and the 2-((meth)allyloxymethyl)acrylic acid derivative is:

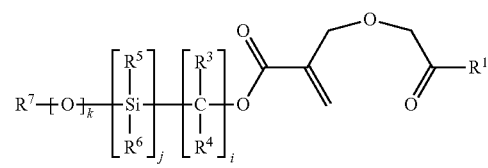

wherein $R^1$ represents H or $CH_3$, $R^3$, $R^4$, and $R^7$ each represent a hydrogen atom or an alkyl group, $R^5$ and $R^6$ each represent an alkyl group, an alkoxide group, or a siloxane group, "i" represents an integer of from 1 to 3, "j" represents an integer of 1 or more, and "k" represents 0 or 1.

5. The method of producing a 2-((meth)allyloxymethyl)acrylic acid derivative according to claim 4, wherein the component A has a water content of 0.5 wt % or less.

6. The method of producing a 2-((meth)allyloxymethyl)acrylic acid derivative according to claim 4, wherein the component A is obtained through a drying step with a spray dryer.

* * * * *